(12) United States Patent
Uchida et al.

(10) Patent No.: US 6,878,558 B2
(45) Date of Patent: Apr. 12, 2005

(54) WHOLE BLOOD IMMUNOASSAY

(75) Inventors: Shinya Uchida, Kobe (JP); Aya Konishi, Kobe (JP); Tsuneyoshi Torii, Kobe (JP); Kazuhiro Nakashima, Miki (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 09/915,580

(22) Filed: Jul. 27, 2001

(65) Prior Publication Data

US 2002/0031791 A1 Mar. 14, 2002

(30) Foreign Application Priority Data

Jul. 27, 2000 (JP) ........................................ 2000-226270

(51) Int. Cl.⁷ ........................ G01N 33/543; G01N 33/00
(52) U.S. Cl. .................... 436/518; 436/69; 436/522; 435/7.1; 422/73
(58) Field of Search .................. 435/7.1, 5.7, 99, 435/267, 262, 259, 270, 272, 829, 317, 264; 436/518, 522, 69, 8–18, 63, 534, 536, 538, 805; 422/73; 356/335, 336

(56) References Cited

U.S. PATENT DOCUMENTS

| | | | | |
|---|---|---|---|---|
| 4,830,969 A | * | 5/1989 | Holmes | 435/259 |
| 4,851,329 A | * | 7/1989 | Cohen et al. | 435/5 |
| 5,527,714 A | * | 6/1996 | Kosako | 436/534 |
| 5,567,627 A | * | 10/1996 | Lehnen | 436/518 |
| 5,646,001 A | * | 7/1997 | Terstappen et al. | 435/7.21 |
| 6,030,845 A | * | 2/2000 | Yamao et al. | 436/533 |

FOREIGN PATENT DOCUMENTS

| JP | 60047962 A2 | * | 3/1985 | ......... G01N/33/543 |
|---|---|---|---|---|
| JP | A1048214 | | 2/1998 | |

OTHER PUBLICATIONS

Bester et al., "Cholate and pH reduce Interference by Sodium Dodecyl Sulfate in the Determination of DNA with Hoechst." Analytical Biochemistry, vol. 223, No. 2, pp. 229–305, 1994.*

H.M. Shapiro, "Practical flow cytometry", 1995, Wiley-Liss, New York XP002266284, Chapter 1.

* cited by examiner

Primary Examiner—Long V. Le
Assistant Examiner—Lisa V. Cook
(74) Attorney, Agent, or Firm—Birch, Stewart, Kolasch & Birch, LLP

(57) ABSTRACT

A whole blood immunoassay includes the steps of mixing a whole blood sample with sensitized insoluble carrier particles to cause an immune agglutination; diluting the resulting agglutination mixture with an aqueous solution containing an erythrocyte lysing agent to lyse erythrocytes, thereby preparing an assay sample; and determining a degree of agglutination of the assay sample.

13 Claims, No Drawings

WHOLE BLOOD IMMUNOASSAY

CROSS-REFERENCE TO RELATED APPLICATION

This application is related to Japanese Patent Application No. 2000-226270 filed on Jul. 27, 2000, whose priority is claimed under 35 USC § 119, the disclosure of which is incorporated by reference in its entirety.

BACKGROUND OF THE INVENTION

1. Field of the Invention

The present invention relates to a whole blood immunoassay, more particularly a whole blood immunoassay by use of a particle agglutination.

2. Description of Related Art

For immunoassay on infection disease-related test items, serum has been used as a sample to be tested. However, it takes at least about 30 minutes to separate serum from whole blood, including time for blood coagulation and time for subsequent centrifugation.

Typical examples of immunoassay include a radioimmunoassay (RIA), an enzyme immunoassay (EIA), a particle agglutination immunoassay and a counting immunoassay. However, the RIA and the EIA need B(Bound form)/F(Free form) separation after antigen-antibody reaction, and therefore, require time and labor before the results of the assay are obtained.

The particle agglutination immunoassay is advantageous in that it requires only the mixing of a sample to be tested with a suspension of insoluble carrier particles (e.g., latex) sensitized with an antibody or an antigen. It does not require the B/F separation and can be performed by simple operation.

In recent years, however, highly accurate simple immunoassay techniques are demanded. Particularly it has become necessary to judge rapidly whether or not a patient is infected with virus hepatitis, HIV or the like, for example, in the case of emergency operation. Accordingly, it is demanded that assay time from collection of blood up to obtainment of assay results be shortened.

Taking the shortening of the assay time into consideration, it is more desirable to use whole blood collected from a patient than to use serum, as a sample for immunoassay. However, when whole blood is used, the presence of blood cells interferes with the detection of a degree of agglutination of particles.

In view of this, for example, Japanese Unexamined Patent Publication No. HEI 10(1998)-48214 discloses a whole blood assay using a conventional latex agglutination method. According to this disclosure, a whole blood sample is hemolyzed with a surfactant and the resulting sample is tested by a latex turbidimetric immunoassay.

However, this assay has a problem in that the surfactant, which needs to be used in a sufficient concentration for hemolysis, affects the antigen-antibody reaction and a sufficient response cannot be obtained.

SUMMARY OF THE INVENTION

An object of the present invention is to provide a whole blood immunoassay by which the interference of blood cells is avoided without any influence on antigen-antibody reaction.

The present invention provides a whole blood immunoassay comprising the steps of mixing a whole blood sample with sensitized insoluble carrier particles to cause an immune agglutination; diluting the resulting agglutination mixture with an aqueous solution containing an erythrocyte lysing agent to lyse erythrocytes, thereby preparing an assay sample; and determining a degree of agglutination of the assay sample.

These and other objects of the present application will become more readily apparent from a further detailed description given hereinafter. However, it should be understood that the following detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

In the whole blood immunoassay of the present invention, the whole blood sample means blood collected from a human being or other animals but not subjected to serum or plasma separation. However, before the immunoassay of the present invention is carried out, the whole blood sample may be anticoagulated with an anticoagulant and/or diluted with a reaction buffer.

As the anticoagulants used for anticoagulating the sample, usable are those usually used for blood tests such as EDTA salt, citrates and the like. The reaction buffer is not particularly limited, and usable are a phosphate buffer, a Tris-HCl buffer and the like, for example. The pH of the reaction buffer may suitably be about pH 6 to 8.5. To the reaction buffer, a substance suppressing a non-specific reaction, a sensitizer and the like may be added as required. The mixture of the whole blood with the reaction buffer may be for preparation for the subsequent immune agglutination. When the whole blood is diluted with the reaction buffer, the dilution ratio may suitably be about 5 to 100 (by volume) and may preferably be 10 to 50. Temperature and time at which and during which the whole blood is mixed with the reaction buffer may suitably be about 20 to 50° C. and about 1 to 5 minutes.

The insoluble carrier particles may be particles immunized, i.e., sensitized with an antigen or antibody. As materials for the particles, synthetic polymers, typically polystyrene latex or the like may be mentioned, for example.

The size of the insoluble carrier particles is not particularly limited and any known insoluble carrier particles may be used. For example, the size may be about 0.1 to 20 $\mu$m in diameter, preferably about 0.1 to 1.0 $\mu$m in diameter. The particles preferably have a uniform diameter.

The insoluble carrier particles may be sensitized by a method known in the field of art, for example, by physical adsorption, chemical binding, etc. The antigen or antibody used for sensitizing the particles is not particularly limited so long as it can be detected by utilizing antigen/antibody reaction. The insoluble carrier particles are usually used in the form of a suspension in a solvent. The solvent may suitably be water, the above-mentioned buffer or the like. The mixture ratio of the insoluble carrier particles to the solvent is suitably about 0.1 to 1w/v %.

As regards the immune agglutination, a latex suspension containing the sensitized insoluble carrier particles is added to the whole blood sample optionally diluted with the reaction buffer so that antigen/antibody reaction takes place. Here, the mixture ratio of the sample to the insoluble carrier particles (or the mixture ratio of the diluted whole blood sample to the latex suspension) may be about 1:5 to 1:20, for example. The reaction temperature is suitably 20 to 50° C., and the reaction time is suitably 15 seconds to 20 minutes.

As the erythrocyte lysing agent contained in the aqueous solution used for diluting the resulting agglutination mixture, suitable agents that can be used are those capable of not only destroying the membrane of erythrocytes but also dissolving or contracting the membrane. For example, usable are surfactants usually used in the field of counting blood cells for lysing erythrocytes. Particularly, water-soluble surfactants may be mentioned. The water-soluble surfactants may be cationic, anionic, non-ionic or ampholytic. Among these, those having a stronger hydrophobic nature in a hydrophobic part (a larger carbon number) are more preferable because they have a greater ability to lyse erythrocytes.

Examples of cationic surfactants include alkyltrimethylammonium salts and alkylpyridinium salts.

Examples of anionic surfactants include alkyl sulfate (e.g., sodium dodecyl sulfate).

Examples of ampholytic surfactants include alkyl betaine acetates.

Examples of non-ionic surfactants include polyoxyethylenealkyl ethers, polyoxyethylenealkenyl ethers and polyoxyethylenealkylphenyl ethers.

The erythrocyte lysing agent is suitably used 2 to 10000 ppm in the aqueous solution for diluting the agglutination mixture.

The aqueous solution may also contain a salt such as sodium chloride and/or a buffer in addition to the erythrocyte lysing agent. In such cases, the amount of a substance contained may be adjusted as required according to the above-mentioned pH and the like.

In the present invention, after the immune agglutination, erythrocytes are lysed for avoiding their interference with determination before measurement. In an assay as disclosed by Japanese Unexamined Patent Publication No. HEI 10(1998)-48214 in which antigen/antibody reaction is performed after the lysis of erythrocytes. In the presence of the surfactant in a large amount, the antigen/antibody reaction is influenced. In order to decrease the concentration of the surfactant used, the whole blood sample needs to be reduced or diluted, which in turn decreases the concentration of an antigen or antibody to be involved in the antigen/antibody reaction and results in a poor response. However, if the antigen/antibody reaction is firstly performed under the above-mentioned condition, the antigen/antibody reaction itself is not only affected by the surfactant but also proceeds necessarily and sufficiently. Furthermore, it is possible to detect particles without destroying an antigen/antibody reaction composite (agglutination mixture).

A method of determining the degree of agglutination of the assay sample after erythrocytes are lysed may be any known method without particular limitation. Usable is a known apparatus for determining the degree of agglutination. For example, in the case of the turbidimetric immunoassay, a spectrophotometer may be used. In the case of the counting immunoassay, a measuring apparatus using the principle of flow cytometry may be used and a commercially available flow cytometer may be used.

A PAMIA series produced by SYSMEX Corporation provides apparatuses for counting immunoassay. This series is suitable because a single apparatus can perform a set of operations from mixing a sample with a buffer to calculating the degree of agglutination automatically.

The determination of the degree of agglutination using a flow cytometer can be done as follows:

Agglutinated particles and unagglutinated particles contained in the prepared assay sample are extruded little by little into a laminar flow of a sheath liquid formed in a flow cell. The particles pass through the center of the flow cell one by one in line.

The particles passing through the flow cell are irradiated with laser light. After passing through the flow cell, the laser light is stopped by a beam stopper. Only forward scattered light is received by a photo diode. As the laser light, light having a wavelength of 310 to 1285 nm may be used, for example, 488 nm, 680 nm, 780 nm, 860 nm, 980 nm and the like. Besides the forward scattered light, side scattered light or both the side scattered light and the forward scattered light may be detected as scattered light.

When a particle crosses the laser light, a scattered light pulse is generated which has an intensity according to the volume of the particle. The pulse is received by a light-receiving unit. Usually, the scattered light pulse received is converted to an electric pulse. The electric pulse provides information about the particle size distribution of the particles. That is, the electric pulse has an intensity according to the volume of the particle entering within the laser light, which particle may be a single particle unagglutinated, two particles agglutinated, three or more particles agglutinated, a blood cell itself, or the like.

The electric pulses are distinguished according to their intensity, and unagglutinated particles and agglutinated particles are counted. For counting these particles, a threshold value is set for distinguishing unagglutinated particles and agglutinated particles on the basis of the intensity of the scattered light. The unagglutinated particles and the agglutinated particles give scattered light of different intensities owing to their different sizes, and can be distinguished from each other. Therefore, the threshold value is set between the unagglutinated particles and the agglutinated particles for distinguishing the unagglutinated particles from the agglutinated particles according to the intensity of scattered light.

Here, the threshold value may be set in situ, at the same time as the scattered light of the assay sample is being measured, on the basis of the measured scattered light data; may be set, after the data is obtained, on the basis of the obtained data; or may be set beforehand as an estimated threshold value from known information, accumulated past data or the like. Particularly, considering measurement errors and reproducibility, the threshold value is preferably set in situ, at the same time as the scattered light of the assay sample is being measured, on the basis of the measured scattered light data.

The unagglutinated particles and agglutinated particles can be distinguished from each other and counted with reference to the threshold value, and the degree of agglutination can be calculated.

The degree of agglutination may be calculated from the number P of the agglutinated particles obtained above and the number M of the unagglutinated particles obtained above out of all counted particles, as the ratio of the agglutinated particles, which have been involved in the antigen/antibody reaction, i.e., $P/(M+P)$, $(M+P=T)$.

If particles not to be counted such as chylomicrons are present in the sample, the particle size distribution of these particles also appear in that of the object insoluble carrier particles. In this case, the particle size distribution of the particles not to be counted can be estimated by interpolation using spline function and subtracted from the particle size distribution including both the object particles and the particles not to be counted. Thereby an approximate correction data only of the object particles can be obtained and utilized for obtaining accurate counts of the agglutinated particles and the unagglutinated particles (see Japanese Patent No. 2912413).

Also, in the present invention, the degree of agglutination is calculated, and then the concentration of the antigen or antibody may be obtained from the calculated degree of agglutination.

The concentration of the antigen or antibody may be obtained by use of a calibration curve which is produced beforehand by obtaining the relationship of the degree of agglutination of the antigen or antibody to a known concentration of the antigen or antibody (preferably, a plurality of degrees of agglutination are determined with changing the concentration).

In the case where a spectrophotometer is used for the determination, a whole blood sample, a buffer and a latex reagent are mixed, and immediately after that, the resulting mixture is diluted with the aqueous solution containing the erythrocyte lysing agent for hemolysis. The hemolyzed sample is put in a measuring cell and irradiated with light to measure absorbance. The wavelength of the light is suitably 600 to 2000 nm. The absorbance at this time is regarded as absorbance at time 0 (i.e., the antigen/antibody reaction has not been taken place yet).

Subsequently, the whole blood sample, the buffer and the latex reagent are mixed and reacted for a given time. The resulting mixture is diluted with the aqueous solution containing the erythrocyte lysing agent for hemolysis. The hemolyzed sample is measured in the same manner as described above. The degree of agglutination can be obtained from a difference between the obtained absorbance and the absorbance at time 0.

EXAMPLE

In this Example, RANREAM HBsAg (produced by SYSMEX Corporation) was used for preparing a sample which was subjected to the latex agglutination and then hemolyzed. PAMIA-30 (produced by Sysmex Corporation) was used for determination.

RANREAM (registered) HBsAg is a reagent kit for detecting an HBs antigen and includes a latex reagent, a buffer, a sample diluent and a calibrator, among which the latex reagent and the buffer were used in this example. The latex reagent is a 0.5% (w/v) suspension of 0.8 $\mu$m polystyrene latex sensitized with an anti-HBs antibody.

Whole blood, 10 $\mu$L, was mixed with 80 $\mu$L of the buffer (pH6) and incubated at 45° C. for a minute. The latex reagent sensitized with the anti-HBs antibody, 10 $\mu$L, was added thereto to start reaction at 45° C.

About 20 seconds after the reaction was started, 19 $\mu$L of the reaction mixture were mixed with 950 $\mu$L of a sheath liquid (200 ppm sodium dodecyl sulfate, 0.3 g/L aqueous solution of sodium chloride) into a 51-fold dilution to lyse erythrocytes and to prepare an assay sample.

The assay sample was introduced to an optical detector of PAMIA-30 to determine the degree of agglutination P/T (%) (T1).

About 15 minutes after the reaction was started, the degree of agglutination P/T (%) (T2) was determined after erythrocytes were lysed, in the same manner as the degree of agglutination P/T (%) (T1). T1 was the degree of agglutination in the early stage of the reaction and was used for judging whether or not the sample was within a measurement range. Usually, T2 is used as the degree of agglutination (agglutination ratio) of the sample.

On the other hand, for a comparison purpose, as a prior-art example, the whole blood sample was first hemolyzed using a buffer including 10000 ppm of sodium dodecyl sulfate necessary for lysing erythrocytes and then subjected to the latex agglutination.

About 20 seconds after the reaction was started, 19 $\mu$L of the reaction mixture were mixed with 950 $\mu$L of a sheath liquid (0.3 g/L aqueous solution of sodium chloride) into a 51-fold dilution to prepare an assay sample.

Further, for reference, the agglutination ratio (P/T) of a serum sample was determined without sodium dodecyl sulfate contained in the buffer and in the sheath liquid.

The results are shown below.

TABLE 1

| | Serum Sample | Present Invention | Prior Art |
|---|---|---|---|
| P/T (%) | 46.03 | 45.38 | 6.00 |

As shown above, it has been confirmed that the antigen/antibody reaction was inhibited by interference of the surfactant in the prior-art example while the reaction was not inhibited and an accurate determination was realized in the present invention.

According to the present invention, by diluting the sample with the aqueous solution containing the surfactant to lyse erythrocytes immediately before measurement, the antigen/antibody reaction can be carried out without interference of the surfactant, and a highly sensitive measurement can be performed.

What is claimed is:

1. A whole blood immunoassay comprising the steps of:
   mixing a whole blood sample with sensitized insoluble carrier particles to cause an immune agglutination;
   diluting the resulting agglutination mixture with an aqueous solution containing an erythrocyte lysing agent to lyse erythrocytes and form a resulting whole blood sample; and
   determining a degree of agglutination of the resulting whole blood sample.

2. A whole blood immunoassay according to claim 1, wherein the erythrocyte lysing agent is a surfactant.

3. A whole blood immunoassay according to claim 2, wherein the surfactant is sodium dodecyl sulfate.

4. A whole blood immunoassay according to claim 1, wherein the degree of agglutination of the resulting whole blood sample is conducted by flow cytometry.

5. A whole blood immunoassay according to claim 4, further comprising the steps of:
   introducing the resulting whole blood sample including unagglutinated particles and agglutinated particles to a flow cell, irradiating particles passing through the flow cell with laser light, and detecting scattered light generated thereby;
   setting a threshold value for distinguishing unagglutinated particles from agglutinated particles with regard to intensity of the scattered light; and
   distinguishing and counting the unagglutinated particles and the agglutinated particles in reference to the threshold value; and
   calculating the degree of agglutination from the number of unagglutinated particles and the number of agglutinated particles.

6. A whole blood immunoassay according to claim 5, wherein the degree of agglutination is calculated by the number of agglutinated particles P/(the number of agglutinated particles P+the number of unagglutinated particles M).

7. A whole blood immunoassay according to claim 5, wherein the scattered light is forward scattered light.

8. A whole blood immunoassay according to claim 1, wherein the size of the insoluble carrier particles is 0.1 μm to 20 μm.

9. A whole blood immunoassay according to claim 1, wherein a mixture ratio of the whole blood sample to the insoluble carrier particles is 1:5 to 1:20.

10. An immunoassay according to claim 1, wherein, in the immune agglutination of the whole blood sample with the insoluble carrier particles, the reaction temperature is from 20 to 50° C. and the reaction time is from 15 seconds to 20 minutes.

11. A whole blood immunoassay comprising the steps of:
   mixing a whole blood sample, which comprises an antigen and an antibody, with immuno-sensitized insoluble carrier particles to cause an immune agglutination prior to adding a lysing agent;
   diluting the resulting agglutination mixture with an aqueous solution containing an erythrocyte lysing agent to lyse erythrocytes and form a resulting whole blood sample; and
   determining a degree of agglutination of the resulting whole blood sample.

12. The whole blood immunoassay of claim 1, wherein the degree of agglutination of the resulting whole blood sample is determined by a PAMIA apparatus.

13. The whole blood immunoassay of claim 11, wherein the degree of agglutination of the resulting whole blood sample is determined by a PAMIA apparatus.

* * * * *